United States Patent [19]
Hawkins

[11] Patent Number: 5,898,071
[45] Date of Patent: Apr. 27, 1999

[54] DNA PURIFICATION AND ISOLATION USING MAGNETIC PARTICLES

[75] Inventor: Trevor Hawkins, Somerville, Mass.

[73] Assignee: Whitehead Institute for Biomedical Research, Cambridge, Mass.

[21] Appl. No.: 09/002,412

[22] Filed: Jan. 2, 1998

Related U.S. Application Data

[62] Division of application No. 08/309,267, Sep. 20, 1994, Pat. No. 5,705,628.
[51] Int. Cl.$^6$ .............................. C12N 15/10; H01F 1/00
[52] U.S. Cl. .................... 536/25.4; 252/62.51; 435/91.1; 435/975
[58] Field of Search ....................... 536/25.4; 252/62.51; 435/91.1, 975

[56] References Cited

U.S. PATENT DOCUMENTS

| | | | |
|---|---|---|---|
| 4,554,088 | 11/1985 | Whitehead et al. | 252/62.54 |
| 4,628,037 | 12/1986 | Chagnon et al. | 436/526 |
| 4,672,040 | 6/1987 | Josephson | 436/526 |
| 4,695,393 | 9/1987 | Whitehead et al. | 252/62.54 |
| 4,698,302 | 10/1987 | Whitehead et al. | 435/94 |

FOREIGN PATENT DOCUMENTS

| | | |
|---|---|---|
| 91/12079 | 8/1991 | WIPO . |
| 93/25709 | 12/1993 | WIPO . |

OTHER PUBLICATIONS

H. C. Birnboim and J. Doly, "A Rapid Alkaline Extraction Procedure for Screening Recombinant Plasmid DNA," *Nucleic Acids Research*, 7(6):1513–1523 (1979).

D. Ish–Horowicz and J. F. Burke, "Rapid and Efficient Cosmid Cloning," *Nucleic Acids Research*, 9(13):2989–2997 (1981).

K. R. Paithankar and K. S. N. Prasad, "Precipitation of DNA by Polyethylene Glycol and Ethanol," *Nucleic Acids Research* 19(6):1346 (Feb. 6, 1991).

R. P. Alderton, et al., "Magnetic Bead Purification of M13 DNA Sequencing Templates," *Analytical Biochemistry*, 201:166–169 (1992).

"High–Throughput Purification of M13 Templates for DNA Sequencing," *Biotechniques*, 15(3):411–422 (1993).

J. T. Lis, "Fractionation of DNA Fragments by Polyethylene Glycol Induced Precipitation", *Methods in Enzymology*, 65:346–353 (1980).

Hawkins, Trevor, "M13 Single–Strand Purification Using A Biotinylated Probe and Streptavidin Coated Magnetic Beads," *DNA Sequence—J. DNA Sequencing and Mapping*, 3:65–69 (1992).

Hawkins et al., "A Purification and Isolation Using A Solid–Phase," *Nucleic Acids Research*, 22(21):4543–4544 (1994).

*Primary Examiner*—Gary L. Kunz
*Attorney, Agent, or Firm*—Hamilton, Brook, Smith & Reynolds, P.C.

[57] ABSTRACT

A method of separating polynucleotides, such as DNA, RNA and PNA, from a solution containing polynucleotides by reversibly and non-specifically binding the polynucleotides to a solid surface, such as a magnetic microparticle, having a functional group-coated surface is disclosed. The salt and polyalkylene glycol concentration of the solution is adjusted to levels which result in polynucleotide binding to the magnetic microparticles. The magnetic microparticles with bound polynucleotides are separated from the solution and the polynucleotides are eluted from the magnetic microparticles.

13 Claims, No Drawings

DNA PURIFICATION AND ISOLATION USING MAGNETIC PARTICLES

RELATED APPLICATIONS

This application is a Divisional application of U.S. Ser. No. 08/309,267, filed Sep. 20, 1994, now U.S. Pat. No. 5,705,628, the teachings of which are incorporated herein by reference in their entirety.

FUNDING

This invention was made with Government support under NIH Grant #HG00098. The Government has certain rights in the invention.

BACKGROUND OF THE INVENTION

Preparation and manipulation of high quality DNA is a vital step in molecular biology. Although there are many methods reported for single and double stranded DNA isolations (Bankier, A. et al., *Meth. Enz.*, 155:52–93 (1988); Birnboim, H. et al., *Nucl. Acids Res.*, 7:1513 (1979); Ish-Horowicz, D. et al., *Nucl. Acids Res.*, 9:2989 (1981); Kristensen, T. et al., *Nucl. Acids Res.*, 15:5507–5516 (1987); Smith, V. et al., *DNA Seq. and Mapping*, 1:73–78 (1990)), there are few procedures that are rapid, low cost and procedurally identical for all DNA types, from PCR product to single copy BAC clone.

SUMMARY OF THE INVENTION

The present invention is a method of binding polynucleotides non-specifically and reversibly to a solid phase which reversibly binds polynucleotides, such as magnetic microparticles whose surfaces are coated with a functional group, such as a carboxyl group. The polynucleotides can be DNA, RNA or polyamide nucleic acids (PNAs). The method comprises combining the solid phase, such as magnetic microparticles and a solution containing polynucleotides. The salt concentration and polyalkylene glycol concentration of the resulting combination are adjusted to concentrations suitable for binding polynucleotides to the surface of the solid phase, such as to surfaces of the magnetic microparticles; as a result, polynucleotides are bound non-specifically to the magnetic microparticles.

The present invention also relates to a method of separating polynucleotides, such as DNA, RNA and PNA, from a solution containing polynucleotides. The method comprises binding polynucleotides non-specifically to a solid surface, such as to magnetic microparticles, as described above, washing the resulting bound polynucleotides with a high ionic strength buffer, and eluting the polynucleotides with a low ionic strength elution buffer.

The method described herein is useful to separate double stranded (ds) or single stranded (ss) polynucleotides (e.g., DNA, RNA, PNA) of virtually any size and from a wide variety of sources. For example, the present method can be used to separate DNA present in a transfected host cell, DNA resulting from an amplification process (e.g., polymerase chain reaction, PCR) and DNA in gels, such as agarose gels. In addition, biochemical reactions and sequencing can be performed on DNA bound to the magnetic microparticles.

The present invention also relates to a kit comprising magnetic microparticles and a binding buffer which contains a suitable salt and polyalkylene glycol at concentrations suitable for reversibly binding polynucleotide onto solid surfaces, such as to the surfaces of magnetic microparticles. The kit may additionally comprise a suitable wash buffer, elution buffer, reagents for preparing such buffers or reagents for preparing a cleared lysate.

Because the method of the present invention is useful with both single and double stranded polynucleotides, as well as a wide range of polynucleotide fragment sizes, it has applicability in essentially any context in which polynucleotide separation is desired. In addition, this permits the standardization of manipulations and isolation carried out with polynucleotides. The present method simplifies the isolation of cloned DNA from lysate by obviating the need for centrifugation and produces a plasmid ready for sequencing and further characterization and processing. The present method also has the advantage that is fast, thus allowing for the rapid throughput in isolating polynucleotides, low cost and simple to perform and produces high yields of polynucleotides. These properties, coupled with its applicability to many procedures useful in molecular biology, make the method amenable to automation.

DETAILED DESCRIPTION OF THE INVENTION

As described herein, Applicant has shown that polynucleotides bind reversibly and non-specifically to solid surfaces, such as certain magnetic microparticles, at certain concentrations of salt and polyalkylene glycol. As a result, a method for convenient and rapid separation of polynucleotides, such as DNA, RNA and PNA, from other biomolecules, such as proteins, monosaccharides, polysaccharides, lipids and RNA and from cellular components, such as cell membranes, is available. Also available is a method for separation of polynucleotides on the basis of size. The following is a description of the present invention with reference to polynucleotides as exemplified by DNA. It is to be understood that the present invention is also useful for separation of RNA and PNAs in a similar manner. Because small polynucleotides require higher salt concentrations for strong binding to the microparticles, salt concentrations can be selectively manipulated to release polynucleotides bound to magnetic microparticles on the basis of size.

One embodiment of the present invention is a method of separating DNA from a solution containing DNA. The method comprises a first step of reversibly binding DNA non-specifically to a solid surface, such as magnetic microparticles whose surfaces are coated with functional groups. In the method, the magnetic microparticles are combined with a solution of DNA, after which the salt concentration and the polyethylene glycol concentration of the resulting combination are adjusted to a concentration suitable for binding DNA onto the surface of the magnetic particles. In one embodiment, sufficient salt and polyethylene glycol are added to the solution containing magnetic microparticle-bound DNA to result in a final concentration of from about 0.5 M to about 5.0 M salt and from about 7% to about 13% polyethylene glycol. As a result, DNA is bound non-specifically to the surfaces of the magnetic microparticles. Subsequently, the magnetic microparticles in the resulting combination are separated from the supernatant. The magnetic microparticles having DNA bound thereto can, optionally, be washed with a suitable wash buffer before they are contacted with a suitable elution buffer, to elute and separate the DNA from the magnetic microparticles. In a final step, the magnetic particles are separated from the elution buffer, which contains the polynucleotide, in solution. The magnetic microparticles are separated from the elution buffer by, for example, filtration or applying a magnetic field to draw down the microparticles.

Solid surfaces which bind DNA and have sufficient surface area to permit efficient binding can be used in the present invention. Microparticles, fibers, beads and supports contain suitable surfaces. Generally, magnetic microparticles are used in the present invention. As used herein, "magnetic microparticles" are microparticles which are attracted by a magnetic field. The magnetic microparticles used in the method of the present invention comprise a magnetic metal oxide core, which is generally surrounded by an adsorptively or covalently bound silane coat to which a wide variety of bioaffinity adsorbents can be covalently bound through selected coupling chemistries, thereby coating the surface of the microparticles with functional groups. The magnetic metal oxide core is preferably iron oxide, wherein iron is a mixture of $Fe^{2+}$ and $Fe^{3+}$. The preferred $Fe^{2+}/Fe^{3+}$ ratio is preferably 2/1, but can vary from about 0.5/1 to about 4/1. Suitable amino silanes useful to coat the microparticle surfaces include p-aminopropyltrimethoxysilane, N-2-aminoethyl-3-aminopropyltrimethoxysilane, triaminofunctional silane $(H_2NCH_2—Nh—CH_2CH_2—NH—CH_2—Si—(OCH_3)_3$, n-dodecyltriethoxysilane and n-hexyltrimethoxysilane. Methods of preparing these microparticles are described in U.S. Pat. Nos. 4,628,037, 4,554,088, 4,672,040, 4,695,393 and 4,698,302, the teachings of which are hereby incorporated by reference into this application in their entirety. These patents disclose other amino silanes which are suitable to coat the iron oxide core and which are encompassed by this invention. Magnetic microparticles comprising an iron oxide core, as described above, without a silane coat (BioMag Iron Oxide particles available from PerSeptive Diagnostics, Division of PerSeptive Biosystems, Catalog Number 8-4200) can also be used in the method of the present invention.

As used herein, the term "functional group-coated surface" refers to a surface which is coated with moieties which each have a free functional group which is bound to the amino group of the amino silane on the microparticle; as a result, the surfaces of the microparticles are coated with the functional group containing moieties. The functional group acts as a bioaffinity absorbent for DNA in solution. In one embodiment, the functional group is a carboxylic acid. A suitable moiety with a free carboxylic acid functional group is a succinic acid moiety in which one of the carboxylic acid groups is bonded to the amine of amino silanes through an amide bond and the second carboxylic acid is unbonded, resulting in a free carboxylic acid group attached or tethered to the surface of the magnetic microparticle. Carboxylic acid-coated magnetic microparticles are commercially available from PerSeptive Diagnostics (BioMag COOH, Catalog Number 8-4125). Other suitable functional groups which can used for coating the surface of the magnetic microparticles include, but are not limited to thiol groups (microparticles with thiol group coating are commercially available from PerSeptive Diagnostics, Division of PerSeptive Biosystems, Catalog Number 8-4135) and streptavidin (microparticles with a streptavidin coating are commercially available from PerSeptive Diagnostics, BioMag Steptavidin, Catalog Number 8-MB4804). As used herein, magnetic microparticles coated with thiol groups or streptavidin bind DNA less efficiently than carboxyl group-coated microparticles.

The importance of having functional groups coat the surface of microparticles used is demonstrated by the observation that polymer encapsulated magnetic microparticles do not bind DNA in the method of the present invention. Polymer encapsulated microparticles are commercially available from Dynal, Incorporated, Dynabeads M-280, (Catalog Number 112.06). The advantage of having a metal oxide core is illustrated by the observation that washing the magnetic microparticles with EDTA, which removes some of the iron, reduces the ability of the magnetic microparticles to bind DNA. Microparticles with a cellulose/iron oxide core, which are commercially available from Amersham International (Catalog Number NIF 876) did not bind DNA in the method of the present invention as it is described herein.

Magnetic microparticles useful in the present method can be a variety of shapes, which can be regular or irregular; preferably the shape maximizes the surface areas of the microparticles. The magnetic microparticles should be of such a size that their separation from solution, for example by filtration or magnetic separation, is not difficult. In addition, the magnetic microparticles should not be so large that surface area is minimized or that they are not suitable for microscale operations. Suitable sizes range from about $0.1\mu$ mean diameter to about $100\mu$ mean diameter. A preferred size is about $1.0\mu$ mean diameter. Suitable magnetic microparticles are commercially available from PerSeptive Diagnostics and are referred to as BioMag COOH (Catalog Number 8-4125). "Non-specific DNA binding" refers to binding of different DNA molecules with approximately the same affinity to magnetic microparticles, despite differences in the DNA sequence or size of the different DNA molecules. A polynucleotide can be DNA, RNA or a synthetic DNA analog such as a PNA (Nielsen et al., *Science*, 254:1497 (1991)). "Non-specific DNA binding" refers to binding of different DNA molecules with approximately the same affinity to magnetic microparticles despite differences in the nucleic acid sequence or size of the different DNA molecules. "A solution containing DNAs" can be any aqueous solution, such as a solution containing DNA, RNA and/or PNAs. Such a solution can also contain other components, such as other biomolecules, inorganic compounds and organic compounds. The solution can contain DNA which is the reaction product of PCR amplification. The solution can also be a cleared lysate. A "lysate", as used herein, is a solution containing cells which contain cloned DNA and genomic DNA and whose cell membranes have been disrupted, with the result that the contents of the cell, including the DNA contained therein, are in the solution. A "cleared lysate" is a lysate in which the chromosomal DNA, proteins and membranes of the host cells have been selectively removed, such as by chemical treatment or centrifugation of the lysate, thereby leaving a solution containing plasmid DNA. RNase can be added to create a "cleared lysate" free of RNA, thereby allowing DNA to bind to the magnetic microparticles free from RNA. Methods of creating a cleared lysate are well-known in the art. For example, a cleared lysate can be produced by treating the host cells with sodium hydroxide or its equivalent (0.2 N) and sodium dodecyl sulfate (SDS) (1%). This method of creating a cleared lysate is described in detail in Birnboim and Doly, *Nucl. Acids Res.*, 7:1513 (1979) Horowicz and Burke, *Nucleic Acids Research* 9:2989 (1981), the teachings of which are hereby incorporated in their entirety into this reference.

A host cell is any cell, such as a bacterial cell such as *E. coli*, a mammalian cell or a yeast cell which contains exogenous or foreign DNA, in addition to genomic DNA. The foreign DNA may be introduced directly into the host cell by means known to one of ordinary skill in the art. Examples of foreign DNA introduced directly into a host cell include bacterial artificial chromosomes (BAC), yeast artificial chromosomes (YAC), plasmids, cosmids and P1. BACs are particularly difficult to separate and purify from cleared lysates due to their low concentrations in the lysates. (Shizuya et al.) However, BACs are readily separated by the method of the present invention. Alternatively, the plasmid DNA may be introduced into the host cell by a phage into which the plasmid DNA has been packaged. Suitable plasmid DNAs which can be packaged into a phage include a cosmid or P1. Host cells containing foreign DNA introduced by any method are referred to as transfected host cells.

The solution with which the magnetic microparticles is combined may also contain single stranded polynucleotides. For example, the present invention is useful to separate polynucleotides from a solution which is the supernatant from a recombinant DNA-containing M13 bacteriophage isolate which had been used to infect bacterial host cells. The host cells are removed from the supernatant by filtration (Kristensen, et al., *Nucl. Acids Res.*, 15:550–16 (1987)) or by binding the host cells to amine coated surfaces (Hou and Zaniewski, *Biochem*, 12:315 (1990)). Single stranded DNA is released from the M13 bacteriophage into the solution by adding SDS to a final concentration of about 0.3% to about 3%, preferably about 1% and at a temperature from about 60° C. to about 100° C., preferably 80° C.

The DNA-containing solution may also be an agarose solution. For example, a mixture of DNA is separated, according to methods known to one skilled in the art, such as by electrophoresis on an agarose gel. A plug of agarose containing DNA of interest can be excised from the gel and added to 1–10 volumes of 0.5×SSC (0.75 M NaCl, 0.0075 M Sodium Citrate, pH 7.0) preferably 4 volumes. The mixture is then melted at a temperature of from about 60° C. to about 100° C., preferably at about 80° C. for about one to about twenty minutes, preferably ten minutes, to create an agarose solution containing DNA.

As described above, the second step of the present method of binding DNA non-specifically to magnetic microparticles having a functional group-coated surface (e.g., a carboxyl-group-coated surface) comprises adjusting the salt concentration and the polyalkylene glycol concentration of the combination to a concentration of each suitable for binding DNA reversibly onto the surface of the magnetic particles. Suitable polyalkylene glycols include polyethylene glycol (PEG) and polypropylene glycol. Generally, PEG is used. A sufficient quantity of a salt and a sufficient quantity of PEG are combined with the combination of magnetic microparticles and DNA-containing solution to produce a final salt concentration of from about 0.5 M to about 5.0 M and a final PEG concentration of from about 7% to about 13%. At appropriate concentrations of the two, DNA binds non-specifically to the surface of the magnetic microparticles. The binding of the DNA to the magnetic microparticles is rapid; it is generally complete within thirty seconds.

Salts which have been found to be suitable for binding DNA to the microparticles include sodium chloride (NaCl), lithium chloride (LiCl), barium chloride ($BaCl_2$), potassium (KCl), calcium chloride ($CaCl_2$), magnesium chloride ($MgCl_2$) and cesium chloride (CeCl). In one embodiment sodium chloride is used. The wide range of salts suitable for use in the method indicates that many other salts can also be used and can be readily determined by one of ordinary skill in the art. Yields of bound DNA decrease if the salt concentration is adjusted to less than about 0.5 M or greater than about 5.0 M. The salt concentration is preferably adjusted to about 1.25 M.

The molecular weight of the polyethylene glycol (PEG) can range from about 6000 to about 10,000, with a molecular weight of about 8000 being preferred. The concentration of PEG is preferably adjusted to about 10%. Although concentrations of PEG as low as 7% and as high as 13% can be used, yields of bound DNA drop as the concentration of PEG deviates from 10%.

The method of the present invention is useful to separate DNA from a solution containing polynucleotide. As discussed above, the method comprises binding DNA nonspecifically and reversibly to magnetic microparticles having a functional group coated (e.g., carboxyl-coated) surface. The microparticles are then separated from the supernatant, for example by applying a magnetic field to draw down the magnetic microparticles. The remaining solution, i.e. supernatant, can then be removed, leaving the microparticles with the bound DNA. Once separated from the supernatant, the DNA can be removed from the magnetic microparticles particles by washing with a suitable elution buffer. As a result, an elution buffer containing unbound DNA and magnetic microparticles is produced. An elution buffer is any aqueous solution in which the salt concentration and polyalkylene concentration are below the ranges required for binding of DNA onto magnetic microparticles, as discussed above. In addition, sucrose (20%) and formamide (100%) solutions can be used to elute the DNA. A preferred eluent is water. Elution of the DNA from the microparticles occurs in thirty seconds or less when an elution buffer of low ionic strength, for example water, is used. Once the bound DNA has been eluted, the magnetic microparticles are separated from the elution buffer that contains the eluted DNA. Preferably, the magnetic microparticles are separated from the elution buffer by magnetic means, as described above. Other methods known to those skilled in the art can be used to separate the magnetic microparticles from the supernatant; for example, filtration can be used.

Yields of DNA following elution typically approach 100% when the magnetic microparticles are used in excess.

In one embodiment, the magnetic microparticles with bound DNA are washed with a suitable wash buffer solution before separating the DNA from the microparticles by washing with an elution buffer. A suitable wash buffer solution has several characteristics. First, the wash buffer solution must have a sufficiently high salt concentration (i.e., has a sufficiently high ionic strength) that the DNA bound to the magnetic microparticles does not elute off of the microparticles, but remains bound to the microparticles. Suitable salt concentrations are greater than about 1.0 M and is preferably about 5.0 M. Second, the buffer solution is chosen so that impurities that are bound to the DNA or microparticles are dissolved. The pH and solute composition and concentration of the buffer solution can be varied according to the type of impurities which are expected to be present. Suitable wash solutions include the following: 0.5×5 SSC; 100 mM ammonium sulfate, 400 mM Tris pH 9, 25 mM $MgCl_2$ and 1% bovine serum albumine (BSA); and 5 M NaCl. A preferred wash buffer solution comprises 25 mM Tris acetate (pH 7.8), 100 mM potassium acetate (KOAc), 10 mM magnesium acetate ($Mg_2OAc$), and 1 mM dithiothreital (DTT). The magnetic microparticles with bound DNA can also be washed with more than one wash buffer solution. The magnetic microparticles can be washed as often as required to remove the desired impurities. However, the number of washings is preferably limited to two or three in order to minimize loss of yield of the bound DNA. Yields of DNA when the microparticles are used in excess are typically about 80% after washing with a wash buffer and eluting with an elution buffer.

The polynucleotide in the solution with which the magnetic microparticles are combined can be single stranded or double stranded. In addition, the polynucleotide can be homogeneous (i.e. polynucleotides which have the same nucleotide sequence). Alternatively, the polynucleotide can be heterogeneous, (i.e., polynucleotides of differing nucleotide sequences). The polynucleotide can also comprise a DNA library or partial library. The DNA can also comprise molecules of various lengths. For example, DNA fragments of 23 Kb, 9 Kb, 64 Kb, 4 Kb, 2 Kb and 12 bp derived from the electrophoretic separation of a HINDIII cut lambda marker were cut out of the agarose gel and purified by the method of the present invention (see Example 7).

Temperature does not appear to be critical in the method of separating DNA of the present invention. Ambient temperature is preferred, but any temperature above the freezing point of water and below the boiling point of water can be used.

DNA fragments of all sizes bind non-specifically to magnetic microparticles at high ionic strength. High ionic strength refers to salt concentrations greater than 0.5 M. However, smaller fragments of DNA bind with lower affinity than large DNA fragments at lower ionic strengths, for example, about 0.5 M salt concentration and lower.

Another embodiment of the present invention refers to a method of separating a mixture of polynucleotide fragments, such as DNA fragments, based on size. For example, a solution of DNA fragments of different sizes is first combined with magnetic microparticles having a carboxyl group-coated surface under conditions appropriate for non-specific binding of DNA to the magnetic microparticles. The magnetic microparticles are then separated from the supernatant. Optionally, the polynucleotide bound to the magnetic microparticles can be washed with a suitable wash buffer which dissolves bound impurities, but is of high enough ionic strength that the polynucleotide remains attached to the magnetic microparticles. The magnetic microparticles are then washed with an elution buffer of appropriate ionic strength to elute the smaller size polynucleotide fragments, but leave the larger size polynucleotide fragments bound to the magnetic microparticles. The smaller polynucleotide fragments, such as DNA, in the elution buffer can then be isolated in the usual manner or processed further, e.g., subjected to further biochemical reactions. This method has been used to separate PCR primers from the reaction product of a PCR amplification (see Example 6).

The polynucleotide (e.g., DNA) which remains bound to the magnetic particles can then be eluted with a suitable elution buffer. The DNA can then be isolated in the usual manner, or processed further, e.g. subjected to further biochemical reactions. Alternatively, the DNA which remains bound to the magnetic microparticles can be subjected to further size selection by washing with an elution buffer of sufficiently low ionic strength to elute the smaller remaining DNA fragment, but of sufficiently high enough ionic strength to allow the larger remaining polynucleotide fragments to remain bound to the magnetic microparticles.

The separation of polynucleotide fragments (e.g., DNA fragments) based on size can also be accomplished by the method of the present invention by adjusting the PEG concentration, the molecular weight of the PEG used or both.

One embodiment of the present invention is based on the discovery that the magnetic microparticles do not bind enzymes. The magnetic microparticles also do not inhibit the function of enzymes. It is therefore possible to carry out biochemical reactions on DNA bound to the magnetic microparticles, e.g., by exposing the bound DNA to enzymes capable of biochemically modifying the bound DNA under conditions which cause the biochemical modification to take place. Preferably the biochemical reactions are carried out on purified bound DNA (e.g., DNA bound to microparticles which have been separated from a cleared lysate or from a solution in which a biochemical reaction such as PCR was carried out). The purified bound DNA can also be washed with a suitable wash buffer. Because residual salt can inhibit the activity of certain enzymes, it is preferable that washings with high ionic strength salt solutions be followed with a washing with a lower ionic strength solution. The ionic strength of this solution should be low enough that enough residual salt is removed to prevent enzyme inhibition, but not so low that substantial losses in bound DNA result.

In one embodiment, the DNA bound to the magnetic microparticles is digested with a restriction enzyme. The restriction enzyme-digested DNA can then be end-repaired, if necessary, for later ligation to a vector by suitable end-repair enzymes. The end-repaired DNA is typically eluted by the solvent in which the biochemical reaction takes place. Alternatively, the magnetic microparticles are washed with a suitable elution buffer to ensure complete separation of the end-repaired DNA from the microparticles. The magnetic microparticles are then separated from the reaction mixture or elution buffer, preferably by magnetic separation. The solution containing the end-repaired DNA can then be combined with a solution containing a pre-cut vector suitable for ligation to the eluted DNA. The end-repaired DNA can then be ligated to the pre-cut vector by methods known to those skilled in the art. After ligation, the DNA can be transformed into a host cell in the usual way.

In another embodiment, a DNA library is bound to the magnetic microparticles. The DNA bound to the magnetic microparticles will consist of molecules of various sizes and nucleotide sequences (heterogeneous DNA). Specific size fragments can be eluted from the magnetic microparticles by varying the ionic strength of the elution buffer, as described earlier. Alternatively, the concentration, molecular weight or both of the PEG in the elution buffer can be varied, as described earlier, to selectively elute smaller DNA fragments. The DNA fragments which remain bound to the magnetic microparticles can be digested with one or more restriction enzymes and then ligated into a pre-cut vector, as described above. A vector is thereby created in which the DNA insert has a certain size. The vector can then be transformed into a host cell in the usual way.

In another embodiment, the nucleotide sequence of the DNA bound to the magnetic microparticles is determined directly without an elution step which releases the DNA from the magnetic microparticles. DNA is bound to the microparticles as described above. The microparticles with bound DNA are then separated from the supernatant and combined with the reagents used for determining nucleotide sequences under conditions suitable for sequence determination. Suitable reagents and conditions are known to those skilled in the art (See Sanger et al., *Proc. Nat. Acad. Sci.*, 74:5463 (1977) and the ABI 373 Sequencer Manual).

A kit is also provided herein which contains the reagents necessary for separating polynucleotides, such as DNA, RNA and PNAs, from a solution containing polynucleotides by binding the polynucleotides to a solid surface, such as magnetic microparticles having a carboxyl group-coated surface. The kit comprises magnetic microparticles with a carboxyl group-coated surface and a binding buffer. The binding buffer comprises a suitable salt and a suitable polyalkylene glycol which are both present at a concentration suitable for binding DNA to the surface of the magnetic microparticles. In one embodiment, the kit further comprises an elution buffer which is capable of dissolving the polynucleotide, such as DNA, bound to the magnetic microparticles. Alternatively, instead of a binding buffer and/or elution buffer, the kit can comprise the reagents for making the binding and/or elution buffer, to which a known amount of water can be added to create a binding and/or elution buffer of desired concentration.

In another embodiment, the kit further comprises a wash buffer which dissolves impurities bound to the magnetic microparticles, but does not result in elution of the polynucleotide bound to the magnetic microparticles. Alternatively, instead of a wash buffer, the kit can comprise the reagents for making the wash buffer, to which a known amount of water can be added to create a wash buffer of desired concentration.

In yet another embodiment, the kit comprises the reagents necessary for clearing a cell lysate. In a preferred embodiment, the reagents are present in solutions at a concentration suitable for direct use in preparing a cleared lysate without the need for further diluting the solutions.

The present invention will now be illustrated by the following examples, which are not limiting in any way.

General Methodology

The magnetic particles used in the following examples were the carboxyl coated magnetic microparticles from PerSeptive Diagnostics Massachusetts, (Biomag COOH, Catalog Number 8-4125) particles which were 1 $\mu$m in diameter. The particles were stored in phosphate buffered saline (PBS) at a concentration of 20 mg/ml. All agarose gels were run using 1% final agarose (U.S. Biochemical #32827) with 1×TBE buffers. The field strength was 10V/cm with run times from 40–60 minutes. The gels were post-stained with ethidium bromide and visualized under UV.

EXAMPLE 1

Double Stranded DNA Isolation Using the PEG Induced Precipitate Separation

A pUC plasmid (pUC 18, obtained from U.S. Biochemicals, Catalog Number 70070) was purified from its host cell by creating a cleared lysate, reversibly binding the plasmid to the magnetic microparticles, separating the magnetic microparticles and then eluting the DNA. The following procedure was used:

1. Take 1 ml of overnight culture containing the plasmid clone in an Eppendorf™ tube.

2. Create a cleared lysate.

Centrifuge for 2 minutes to pellet the cells.

Pour off the supernatant and resuspend the pellet in 30 $\mu$l Solution 1 (50 mM Glucose, 25 mM Tris.Cl pH 8, 10 mM EDTA pH 8, 100 $\mu$g/ml RNase).

Add 60 $\mu$l Solution 2 (0.2N NaOH, 1% SDS) and mix by shaking. Leave at room temperature for 5 minutes.

Add 45 $\mu$l Solution 3 (3 M KOAc), mix by shaking and leave on ice for 10 minutes.

Centrifuge for 10 minutes and remove 100 $\mu$l of the supernatant to a new Eppendorf tube.

3. Take 10 $\mu$l (@20 mg/ml) carboxyl coated magnetic particles, wash three times in 0.5 M EDTA pH 7.2 and resuspend in 10 $\mu$l 0.5 M EDTA. Add to the cleared lysate.

4. Add 100 $\mu$l of the binding buffer (20% PEG 8000, 2.5 M NaCl) and mix.

5. Allow to incubate at room temperature for 5 minutes.

6. Wash the magnetic particles twice with 5 M NaCl and once with wash buffer (25 mM TrisAcetate pH 7.8, 100 mM KOAc, 10 mM Mg$_2$OAc, 1 mM DTT). There is no need to resuspend the particles during each wash.

7. Resuspend the particles in 50 $\mu$l water and incubate at room temperature for 1 minute.

8. Magnetically separate the particles and remove the DNA to a new tube.

An electrophoretic analysis was done on the cleared lysate after binding to the magnetic microparticles. A complete absence of DNA was observed. An electrophoretic analysis was also done on the elution solution, which showed the purified pUC plasmid.

EXAMPLE 2

Double Stranded DNA Isolation Using the PEG Induced Precipitate Separation Using a Microtitre Plate A pUC plasmid (pUC 18, obtained from U.S. Biochemicals Catalog Number 70070) grown in microtitre plates was purified from its host cell by creating a cleared lysate, reversibly binding the plasmid to the magnetic microparticles, separating the magnetic microparticles and then eluting the DNA. The following procedure was used:

1. Grow a single plasmid clone in the well of a microtitre plate containing 300 $\mu$l of growth media. 96 different clones may be grown in each plate. Grow the plasmids at 37° C. overnight (12–15 hours) shaking at 300 rpm.

2. Create a cleared lysate.

Centrifuge for 10 minutes at 300 rpm to pellet the cells.

Aspirate off the supernatant and resuspend the pellet in 30 $\mu$l Solution 1 (50 mM Glucose, 25 mM Tris Cl pH 8, 10 mM EDTA pH 8, 100 $\mu$g/ml RNase).

Add 60 $\mu$l Solution 2 (0.2N NaOH, 1% SDS) and mix by shaking. Leave at room temperature for 5 minutes.

Add 45 $\mu$l Solution 3 (3 M KOAc), mix by shaking and leave on ice for 10 minutes.

Centrifuge for 15 minutes at 3000 rpm and remove 100 $\mu$l of the supernatant to a new microtitre plate.

3. Take 10 $\mu$l (@ 20 mg/ml) carboxyl coated magnetic particles, wash three times in 0.5 M EDTA pH 7.2 and resuspend in 10 $\mu$l 0.5 M EDTA. Add to each well.

4. Add 100 $\mu$l of the binding buffer to each well (20% PEG 8000, 2.5 M NaCl) and mix.

5. Allow to incubate at room temperature for 5 minutes.

6. Wash the magnetic particles twice with 5 M NaCl and once with wash buffer (25 mM Tris.Acetate pH 7.8, 100 mM KOAc, 10 mM Mg$_2$OAc, 1 mM DTT). There is no need to resuspend the particles during each wash.

7. Resuspend the particles in 50 $\mu$l water and incubate at room temperature for 1 minute.

8. Magnetically separate the particles and remove the DNA to a new microtitre plate.

This example yields 500–800 ng plasmid DNA which is sufficient for thermal cycle DNA sequencing. The advantage of using a microtitre plate is that many samples can be isolated in parallel. As in Example 1, electrophoretic analysis of the cleared lysate after binding to the magnetic microparticles showed no DNA, while electrophoretic analysis of the eluent from microparticles showed purified pUC plasmid.

EXAMPLE 3

Isolating Large DNA Vectors From 500 ml Cultures

A cosmid (pWE15, obtained from Stratagene, Catalog Number 251201) containing a 35 Kb insert and a Bacterial Artificial Chromosome were purified from their host cells by creating a cleared lysate, binding the DNA to the magnetic microparticles, separating the magnetic microparticles from the cleared lysate, and then eluting the DNA. The following procedure was used:

1. Grow a single plasmid clone in 500 ml of growth media. Grow the plasmids at 37° C. overnight (12–15 hours) shaking at 300 rpm.

2. Create a cleared lysate.

Centrifuge for 10 minutes at 4000 rpm to pellet the cells.

Pour off the supernatant and aspirate any further liquid. Resuspend the pellet in 3 ml Solution 1 (50 mM Glucose, 25 mM Tris.Cl pH 8, 10 mM EDTA pH 8, 100 µg/ml RNase).

Add 6 ml Solution 2 (0.2N NaOH, 1% SDS) and mix by shaking. Leave at room temperature for 5 minutes.

Add 4.5 ml Solution 3 (3 M KOAc), mix by shaking and leave on ice for 15 minutes.

Centrifuge for 15 minutes at 5000 rpm and remove 10 ml of the supernatant to a new Falcon tube. (Filter through a 0.45 m filter if there are any visible signs of precipitate).

3. Take 1 ml (@20 mg/ml) carboxyl coated magnetic particles, wash three times in 0.5 M EDTA pH 7.2 and resuspend in 1 ml 0.5 M EDTA. Add to the supernatant.

4. Add 11 ml of the binding buffer to each well (20% PEG 8000, 2.5 M NaCl) and mix.

5. Allow to incubate at room temperature for 15 minutes.

6. Wash the magnetic particles twice with 5 M NaCl and once with wash buffer (25 mM Tris Acetate pH 7.8, 100 mM KOAc, 10 mM $Mg_2OAc$, 1 mM DTT). There is no need to resuspend the particles during each wash.

7. Resuspend the particles in 1 ml water and incubate at room temperature for 1 minute.

8. Magnetically separate the particles and remove the DNA to a new tube.

Electrophoretic analysis of the solutions obtained from washing the magnetic microparticles with water showed purified cosmid cloned containing the 35 Kb insert and the 150 Kb BAC (Bacterial Artificial Chromosome) clone which had been cut with Not1 to excise the 7 Kb vector.

EXAMPLE 4

Single Stranded DNA Isolation from Bacteriophages Using the PEG Induced Precipitate Separation Single stranded DNA from M13 clones using *E. coli* (DH5αF' culture, obtained from U.S. Biochemicals Catalog Number 75112) as a host was isolated by lysing the phage, binding the single stranded DNA to the magnetic microparticles, from separating the magnetic microparticles the supernatant and then eluting the DNA. The following procedure was used:

1. Grow the M13 clones for 6 hours in 500 µl of 1×LB media with a 1/100 dilution an overnight *E.coli* F' culture. Use of the Beckman deepwell plates will facilitate 96 clones being grown at one time.

2. Centrifuge the growth plate at 3000 rpm for 10 minutes to pellet the cells.

3. Add 20 µl of 10% SDS to each well of a Falcon 9311 using a multidispensing pipette.

4. Using a 12 channel pipette, add 100 µl of the phage supernatant to each well, mixing the lysis solution with the supernatant.

5. Incubate the Falcon plate at room temperature for 5 minutes.

6. For a whole plate of 96 clones, remove 1 ml of magnetic particles from the stock and wash three times in 0.5 M EDTA pH 7.2. Take up the washed particles in 1 ml 0.5 M EDTA pH 7.2 and add 10 µl to each well.

7. Add 100 µl of the binding buffer to each well (20% PEG 8000, 2.5 M NaCl) and mix.

8. Incubate the Falcon plate at room temperature for 5 minutes.

9. Wash the magnetic particles twice with 5 M NaCl and once with wash buffer (25 mM Tris Acetate pH 7.8, 100 mM KOAc, 10 mM $Mg_2OAc$, 1 mM DTT). There is no need to resuspend the particles during each wash.

10. Resuspend the particles in 50 µl water and incubate at room temperature for 1 minute.

11. Magnetically separate the particles and remove the DNA to a new microtitre plate.

Electrophoretic analysis of the solution obtained from washing the magnetic microparticles with water showed purified M13 single stranded DNA.

EXAMPLE 5

DNA Sequence from a Plasmid Clone Isolated Using the PEG Induced Precipitate Separation DNA which had been isolated using the procedure described in example 1 was then sequenced using Taq polymerase and fluorescently labelled primers. The DNA sequence was then electrophoresed on an ABI 373A DNA sequence. The clarity of the data, the read length and the lack of ambiguous bases indicated DNA of high purity.

EXAMPLE 6

Selective Removal of DNA from the Solid Phase Based on the Size of the DNA Fragments DNA isolations may also be performed from amplified DNA such as PCR products. One desirable feature of PCR product purification is the removal of residual nucleotides, oil and excess primers (18–25 bp DNA fragments), which may interfere with subsequent reactions. This example demonstrates the isolation of PCR products as well as the selective removal of the primers during the wash stages.

1. PCR amplify the DNA.

2. Bind the DNA products:

Take 10 µl (@20 mg/ml) carboxyl coated magnetic particles, wash three times in 0.5 M EDTA pH 7.2 and resuspend in 10 µl 0.5 M EDTA. Add to the PCR amplifiers.

Add an equal volume of the binding buffer to each reaction (20% PEG 8000, 2.5 M NaCl) and mix.

Allow to incubate at room temperature for 5 minutes.

3. Wash the magnetic particles twice with 5 M NaCl and once with wash buffer (25 mM Tris.Acetate pH 7.8, 100 mM LOAC, 10 mM $Mg_2OAc$, 1 mM DTT). There is no need to resuspend the particles during each wash.

4. Resuspend the particles in 50 µl water and incubate at room temperature for 1 minute.

5. Magnetically separate the particles and remove the DNA to a new tube.

Electrophoretic analysis of the PCR reaction mixture before binding to the magnetic microparticles showed the presence of primers as well as the final product. Electrophoretic analysis after elution from the magnetic microparticles show that the primers were removed from the amplification product.

EXAMPLE 7

DNA Isolation from Agarose Gels Using the PEG Induced Precipitate Separation DNA fragments were isolated directly from molten agarose plugs. A Lambda marker was cut with HINDIII and electrophoresed. Bands corresponding to 23 Kb, 9 Kb, 6 Kb, 4 Kb, and 2 Kb and 125 bp bands were excised and isolated from the molten agarose according to the following procedure.

1. Electrophorese the DNA samples on a 0.5% agarose gel.
2. Cut out the band of interest.
3. Add 4 volumes of 0.5×SSC to the agarose plug and melt for 10 minutes at 80° C.
4. Take 10 μl (@ 20 mg/ml) carboxyl coated magnetic particles, wash three times in 0.5 M EDTA pH 7.2 and resuspend in 10 μl 0.5 M EDTA. Add to the supernatant.
5. Add an equal volume of the binding buffer to each well (20% PEG 8000, 2.5 M NaCl) and mix.
6. Allow to incubate at room temperature for 15 minutes.
7. Wash the magnetic particles twice with 5 M NaCl and once with wash buffer (25 mM Tris Acetate pH 7.8, 100 mM KOAc, 10 mM $Mg_2OAc$, 1 mM DTT). There is no need to resuspend the particles during each wash.
8. Resuspend the particles in 50 μl water and incubate at room temperature for 1 minute.
9. Magnetically separate the particles and remove the DNA to new tube.

Electrophoretic analysis after elution from the magnetic microparticles showed DNA fragments of the sizes excised from the original gel. This approach is rapid and gives the same high yield as the more standard gel extraction applications such as β-agarose (Eppicenter technologies, Wisconsin or Geneclean II (Bio 101 Inc. California).

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of reversibly binding polynucleotides non-specifically to magnetic microparticles, comprising the steps of:
   a) combining magnetic microparticles whose surfaces have bound thereto a functional group which reversibly binds polynucleotide and a solution containing polynucleotides, thereby producing a combination; and
   b) adjusting the salt and polyalkylene glycol concentration of the combination to a concentration suitable for binding the polynucleotide onto the surfaces of the magnetic microparticles, whereby polynucleotide in the solution binds non-specifically to the magnetic microparticles.

2. The method of claim 1, wherein the polynucleotide is DNA and the polyalkylene glycol is polyethylene glycol.

3. The method of claim 2, wherein the polyethylene glycol has a molecular weight of between about 6000 and about 10,000, and wherein the salt is selected from the group consisting of sodium chloride, magnesium chloride, calcium chloride, potassium chloride, lithium chloride, barium chloride and cesium chloride.

4. The method of claim 3, wherein the concentration of the polyethylene glycol is adjusted to between about 5% and about 15% and wherein the concentration of sodium chloride is adjusted to between about 0.5 M and about 5.0 M.

5. The method of claim 4, wherein the concentration of the polyethylene glycol is about 10% and the concentration of sodium chloride is about 1.25 M.

6. A method of binding DNA non-specifically to magnetic microparticles, comprising the steps of:
   a) combining magnetic microparticles whose surfaces have bound thereto a functional group which reversibly binds DNA and a solution containing DNA, thereby producing a combination; and
   b) adjusting the salt and polyethylene glycol concentration of the combination to a concentration suitable for binding the DNA onto the surfaces of the magnetic microparticles, whereby DNA in the solution binds non-specifically to the magnetic microparticles.

7. The method of claim 6, wherein the polyethylene glycol has a molecular weight of between 6000 and 10,000, and wherein the salt is selected from the group consisting of sodium chloride, magnesium chloride, calcium chloride, potassium chloride, lithium chloride, barium chloride and cesium chloride.

8. The method of claim 7, wherein the polyethylene glycol has a molecular weight of about 8000 and the salt is sodium chloride.

9. The method of claim 8, wherein the concentration of the polyethylene glycol is adjusted to between about 5% and about 15% and wherein the concentration of sodium chloride is adjusted to between about 0.5 M and about 5.0 M.

10. The method of claim 9, wherein the concentration of the polyethylene glycol is about 10% and the concentration of sodium chloride is about 1.25 M.

11. The method of claim 10, wherein the DNA solution is a cleared lysate.

12. The method of claim 10, wherein the DNA solution comprises the reaction product of a PCR amplification.

13. The method of claim 10, wherein the DNA solution comprises M13 phage DNA, wherein the host cells have been removed.

* * * * *